United States Patent
Lang et al.

(10) Patent No.: US 7,211,099 B2
(45) Date of Patent: May 1, 2007

(54) MEDICAL INSTRUMENT

(75) Inventors: Dieter Lang, Stockheim (DE); Thomas Hopf, Stockheim (DE)

(73) Assignee: Karl Storz GmbH & Co. KG (DE)

( * ) Notice: Subject to any disclaimer, the term of this patent is extended or adjusted under 35 U.S.C. 154(b) by 338 days.

(21) Appl. No.: 10/457,279

(22) Filed: Jun. 9, 2003

(65) Prior Publication Data

US 2004/0098038 A1    May 20, 2004

Related U.S. Application Data

(63) Continuation of application No. PCT/EP01/14129, filed on Dec. 4, 2001.

(30) Foreign Application Priority Data

Dec. 7, 2000 (DE) ................................ 100 60 769

(51) Int. Cl.
*A61B 17/00* (2006.01)
(52) U.S. Cl. ....................... 606/207; 606/206
(58) Field of Classification Search ............... 81/302, 81/345, 346; 227/175.1; 606/206, 207, 606/208

See application file for complete search history.

(56) References Cited

U.S. PATENT DOCUMENTS

| | | | | |
|---|---|---|---|---|
| 3,814,102 A | * | 6/1974 | Thal | 606/207 |
| 3,840,003 A | * | 10/1974 | Komiya | 600/564 |
| 4,243,047 A | * | 1/1981 | Olsen | 600/564 |
| 4,369,788 A | * | 1/1983 | Goald | 606/207 |
| 4,712,545 A | | 12/1987 | Honkanen | 128/305 |
| 4,721,116 A | * | 1/1988 | Schintgen et al. | 600/564 |
| 4,887,612 A | * | 12/1989 | Esser et al. | 600/564 |
| 5,147,373 A | * | 9/1992 | Ferzli | 606/144 |
| 5,201,759 A | * | 4/1993 | Ferzli | 606/207 |
| 5,217,460 A | * | 6/1993 | Knoepfler | 606/52 |
| 5,282,826 A | * | 2/1994 | Quadri | 606/207 |

(Continued)

FOREIGN PATENT DOCUMENTS

DE    G 90 10 804.3    11/1990

(Continued)

*Primary Examiner*—Anhtuan T. Nguyen
*Assistant Examiner*—Darwin P Erezo
(74) *Attorney, Agent, or Firm*—St. Onge Steward Johnston & Reens LLC

(57) ABSTRACT

The invention relates to a medical instrument, comprising a shaft, the proximal end of which has a handle, with at least two grip pieces and the distal end of which has a tool, with at least two jaw pieces, whereby at least one jaw piece of the tool may be adjusted relative to the at least one other jaw piece for opening and closing, by means a grip piece on the handle, embodied so as to pivot. Each adjustable jaw piece and the corresponding grip piece in the handle, for adjusting the jaw piece, are connected to each other, by means of a pull-/push-rod and each adjustable jaw piece is connected to the pull-/push-rod, by means of a compensation lever. According to the invention, the best possible force transfer with a good cutting feel for the operator may be achieved, whereby the compensation lever is pivotably fixed on one end to the pull-/push-rod and displaceably mounted at the other end in a guide groove, formed in the adjustable jaw piece.

6 Claims, 2 Drawing Sheets

U.S. PATENT DOCUMENTS

| | | | |
|---|---|---|---|
| 5,366,477 A * | 11/1994 | LeMarie et al. | 606/208 |
| 5,383,888 A * | 1/1995 | Zvenyatsky et al. | 606/206 |
| 5,391,180 A * | 2/1995 | Tovey et al. | 600/224 |
| 5,395,375 A * | 3/1995 | Turkel et al. | 606/83 |
| 5,395,386 A | 3/1995 | Slater | 606/170 |
| 5,478,347 A | 12/1995 | Aranyi | 606/170 |
| 5,490,819 A * | 2/1996 | Nicholas et al. | 600/201 |
| 5,507,773 A * | 4/1996 | Huitema et al. | 606/207 |
| 5,514,157 A * | 5/1996 | Nicholas et al. | 606/206 |
| 5,569,299 A * | 10/1996 | Dill et al. | 606/205 |
| 5,590,570 A * | 1/1997 | LeMaire et al. | 74/579 R |
| 5,601,578 A * | 2/1997 | Murphy | 606/148 |
| 5,624,452 A * | 4/1997 | Yates | 606/139 |
| 5,690,673 A * | 11/1997 | Koscher et al. | 606/205 |
| 5,700,276 A * | 12/1997 | Benecke | 606/208 |
| 5,749,893 A * | 5/1998 | Vidal et al. | 606/205 |
| 5,766,205 A * | 6/1998 | Zvenyatsky et al. | 606/206 |
| 5,810,883 A * | 9/1998 | Lang | 606/207 |
| 5,826,776 A | 10/1998 | Schulze et al. | 227/176.1 |
| 5,851,214 A * | 12/1998 | Larsen et al. | 606/170 |
| 5,906,630 A * | 5/1999 | Anderhub et al. | 606/205 |
| 6,019,780 A | 2/2000 | Lombardo et al. | 606/207 |
| 6,270,508 B1 * | 8/2001 | Klieman et al. | 606/147 |
| 6,582,451 B1 * | 6/2003 | Marucci et al. | 606/207 |

FOREIGN PATENT DOCUMENTS

| | | |
|---|---|---|
| DE | G 93 20 450.7 | 9/1994 |
| DE | 195 34 618 A1 | 3/1997 |
| DE | 197 02 079 A1 | 7/1998 |
| DE | 199 06 360 A1 | 8/2000 |
| WO | WO 00/54662 A1 * | 9/2000 |

* cited by examiner

MEDICAL INSTRUMENT

This application is a continuation of pending International Patent Application No. PCT/EP01/14129 filed Dec. 4, 2001, which designates the United States and claims priority of pending German Application No. 100 60 769.1, filed Dec. 7, 2000.

FIELD OF THE INVENTION

The invention relates to a medical instrument with a shaft having on its proximal end a handle consisting of two gripping members and on its distal end a tool consisting of at least two jaw members, whereby at least one jaw member of the tool can be moved for opening and closing by means of one rotatably configured gripping member of the handle with respect to the at least one other jaw member of the tool and where each movable jaw member and the corresponding gripping member of the handle serving to move the jaw member are connected to one another by means of a push-pull rod, so that each movable jaw member is connected with the respective push-pull rod by means of a compensating lever.

Generic instruments link the movable jaw member or members by means of a lever mechanism. The angle between the instrument axis and the line through the rotation point of the jaw member and of the connecting point on the lever is thus selected to be as large as possible. In opening or closing the jaw members, however, there is inevitably a reduction of the angle, which clearly worsens the force transmission. Especially in medical punching machines for tissue it is unknown in which angle position of the jaw members the force must be especially well transmitted, because tissues of variable thickness can be involved.

A generic medical instrument is known, for instance, from DE 199 06 360 A1. In this known construction, between the actuation rod and the rotatable jaw member, a tension rod is mounted serving to pull the jaw member back into the closed position. To open the jaw member, the actuation rod has its tip in contact with a pressure surface of the jaw member and thus presses the jaw member into the open position. In order to allow the actuation rod to contact the pressure surface of the jaw member on the one hand, and on the other hand to allow the jaw member to be closed by the tension rod, the bearing of the tension rod has a longitudinal hole groove on the actuation rod which allows the actuation rod to be displaced without actuating the tension rod. However, this looseness in the actuation rod due to the lack of direct coupling to the tension rod causes an intermediate stage for the operator, in which the cutting sensation is reduced because there is no immediate coupling between the jaw member and the handle connected with the actuation rod.

An additional medical instrument is known from U.S. Pat. No. 4,712,545 A. In this known surgical instrument the movable jaw member is moved on a curved track in the stationary member of the shaft and on an additional curved track to a pull rod. This configuration leads to imaginary rotation points that lie partly outside the instrument shaft. As a result, however, only the lever arm is enlarged—and similar effects can result from like action on the handle—and thus more force is transmitted in each position. However, the more the force parallelogram is extended, the more favorable is the lever ratio, so that in the extreme case even with a large lever arm no more force can be transmitted.

U.S. Pat. No. 6,019,780A, also known from current technology, presents another medical instrument in which the rotation point is displaced outward by means of a track guide. Just as with U.S. Pat. No. 4,712,545 A, with this known instrument the track guide causes an additional friction which reduces the operator's cutting sensation.

On the basis of this state of the art, the aim of the invention is to perfect a medical instrument of the aforementioned type in such a way that the instrument ensures the best possible force transmission with a good cutting sensation for the operator.

This aim is fulfilled by the invention in such a way that the compensating lever, on the one hand, is rotatably secured to the push-pull rod and, on the other hand, is mounted so that it can be pushed in a guide groove configured in the movable jaw member.

This configuration ensures that, for the best possible force transmission, there is a constant lever ratio between the push-pull rod and the movable jaw member, because the compensating lever and the push-pull rod are advantageously rotatable but otherwise are solidly bound to one another. This firm connection, moreover, along with the movable guide of the compensating lever in the movable jaw member, ensures that, in actuating the rotatable grip member, the push-pull rod exerts no pendulum motion that increases friction. In addition, the flat plane construction of the compensating lever on the jaw member in the guide groove makes possible a direct and sensitive force transmission to the movable jaw member.

To improve ease of cleaning and to facilitate installation and repair of the medical instrument, in a preferred embodiment of the invention the compensating lever and the push-pull rod can be removed from the shaft as a unit.

According to a first embodiment of the invention, the compensating lever is shaped like a screw with an essentially circular cross-section.

According to an alternative embodiment of the invention it is proposed that the compensating lever is shaped like a screw with a non-round cross-section.

Finally, with the invention it is proposed that a connection point between the compensating lever and the push-pull rod is installed above a rotation point of the movable jaw member.

BRIEF DESCRIPTION OF DRAWINGS

Additional characteristics and advantages of the invention can be seen in the following description of the associated drawing, in which an embodiment of an inventive medical instrument is illustrated in merely schematic form. The illustrations are as follows.

DETAILED DESCRIPTION OF DRAWINGS

Figure 1:
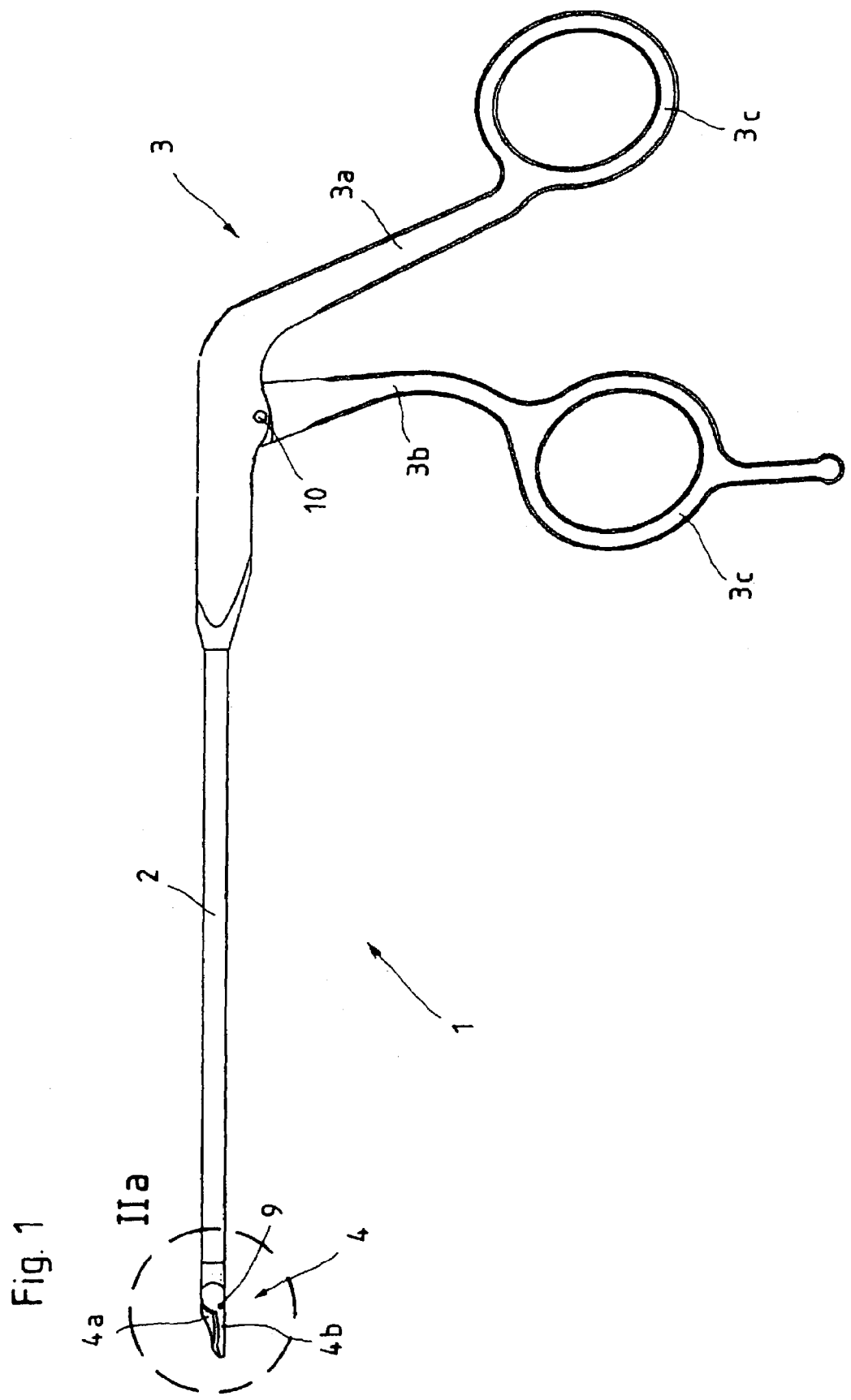
FIG. 1 Lateral view of an inventive medical instrument showing the jaw member in the closed position.

The illustration of FIG. 1 shows a lateral view of a medical instrument 1, whose force transmission mechanism allows multiple uses such as for punch, scissors, needle holder, gripping instrument and the like.

The medical instrument 1 consists essentially of a shaft 2, having on its proximal end a handle 3 consisting of a stationary gripping member 3a and a gripping member 3b that can be rotated with respect to the stationary gripping member 3a. On the distal end of the shaft 2 there is a tool 4, which in the illustrated embodiment, has a movable jaw member 4a and a jaw member 4b that is rigidly connected with the shaft 2.

Figure 2A:
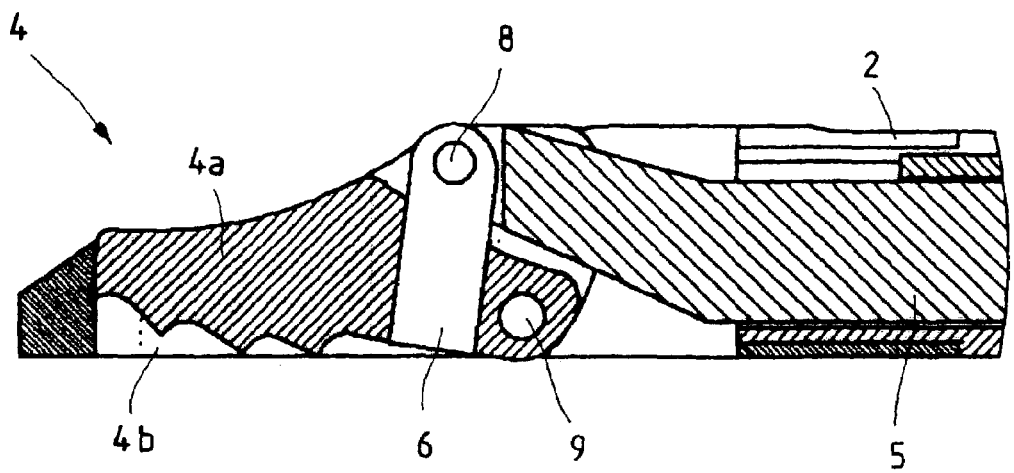
FIG. 2a Enlarged and partly cut-out view of the details IIa according to FIG. 1.
Figure 2B:
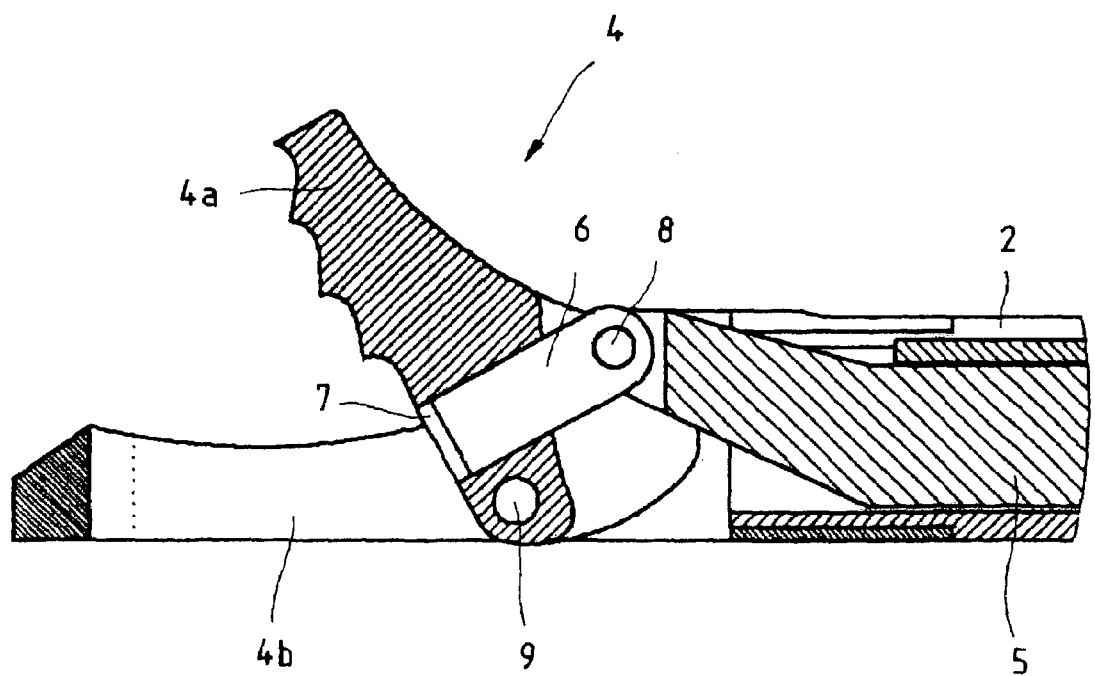
FIG. 2b Sketch according to FIG. 2a, but with the jaw members in the open position.

As can be seen from the detail views in FIGS. 2a and 2b, the movable jaw member 4a of the tool 4 and the rotatable gripping member 3b of the handle 3 are connected to one another by means of a push-pull rod 5 in such a way that, by rotating the gripping member 3b, the movable jaw member 4a can be moved from the closed position (FIGS. 1 and 2a) into the open position (FIG. 2b) or vice versa. In the illustrated medical instrument 1, the shaft 2 is configured as hollow for receiving the push-pull rod 5.

To ensure the best possible force transmission between the handle 3 and the movable jaw member 5a of the tool 4, the push-pull rod 5 and the movable jaw member 4a, as can be seen in particular from FIG. 2b, are connected to one another by means of a compensating lever 6 so that the compensating lever 6 is mounted so that it can be slid in a guide groove 7 configured in the movable jaw member 4a and a connection point 8 is installed between the compensating lever 8 and the push-pull rod 5 above a rotation point 9 of the movable jaw member 4a. The connection of the push-pull rod 5 and the movable jaw member 4a by means of the compensating lever 6 moved slidably in the jaw member 4a allows a uniform lever ratio between the two components 5 and 4a without the risk of a pendulum movement of the push-pull rod 5. Because of this stable lever ratio, the operator always has a good, stable cutting feeling.

To ensure secure action by the gripping members 3a, 3b of the handle 3, this handle has finger grips 3c on its free ends. In the illustrated embodiment, the gripping member 3b can be rotated around a rotation axis 10 with respect to the other, stationary gripping member 3a. The rotation path of the two gripping members 3a, 3b to one another can be shortened by means of a displacement that is not illustrated. It is likewise possible to configure both gripping member 3a, 3b of the handle 3 as rotatable gripping members. By means of the coupling of the rotatable gripping member 3b by means of the push-pull rod 5 and the compensating lever 6 with the movable jaw member 4a, the tool 4 can be opened and closed by actuating the handle 3.

Cleaning and repair of the medical instrument 1 is facilitated by the fact that the push-pull rod 5 and the compensating lever 6 can be removed from the hollow shaft 2 as a complete unit.

Altogether, the illustrated medical instrument 1 is distinguished by the fact that it ensures a uniformly strong force transmission independently of the open or closed position of the jaw members and it is possible to apply this force in controlled doses so that there is no uncontrolled penetration of the jaw members acted on by the force after the severing of hard tissue.

Number key to illustrations

| | |
|---|---|
| 1 | medical instrument |
| 2 | shaft |
| 3 | handle |
| 3 | a stationary gripping member |
| 3b | rotatable gripping member |
| 3c | finger grips |
| 4 | tool |
| 4a | movable jaw member |
| 4b | stationary jaw member |
| 5 | push-pull rod |
| 6 | compensating lever |
| 7 | guide groove |
| 8 | connection point |
| 9 | rotation point |
| 10 | rotation axis |

What is claimed is:

1. Medical instrument with a shaft having on its proximal end a handle comprising gripping members and on its distal end a tool comprising jaw members, where a first jaw member of the tool can be moved to open and close with respect to a second jaw member of the tool by means of a rotatably configured gripping member of the handle, the first jaw member and the rotatably configured gripping member of the handle being connected to one another by means of a push-pull rod, with the first jaw member being connected by a compensating lever with the respective push-pull rod, wherein the compensating lever comprises a first free end and a second free end with a longitudinal axis passing through the first free end and the second free end, with the first free end being mounted exclusively on the push-pull rod and being rotatably secured to this rod, and with the second free end being slidably mounted in a guide groove configured in the first jaw member, the second free end being slideable within the guide groove axially along the longitudinal axis of the compensating lever.

2. Medical instrument according to claim 1, wherein the compensating lever is essentially held in form-locking connection in the guide groove.

3. Medical instrument according to claim 1, wherein the compensating lever and the push-pull rod can be removed from the shaft as a unit.

4. Medical instrument according to claim 1, wherein the compensating lever is shaped like a screw with an essentially circular cross-section.

5. Medical instrument according to claim 1, wherein the compensating lever is shaped like a screw with a non-round cross-section.

6. Medical instrument according to claim 1, wherein in the upright working position a connection point between the compensating lever and the push-pull rod is installed above a rotation point of the first jaw member.

* * * * *